Figure 1:
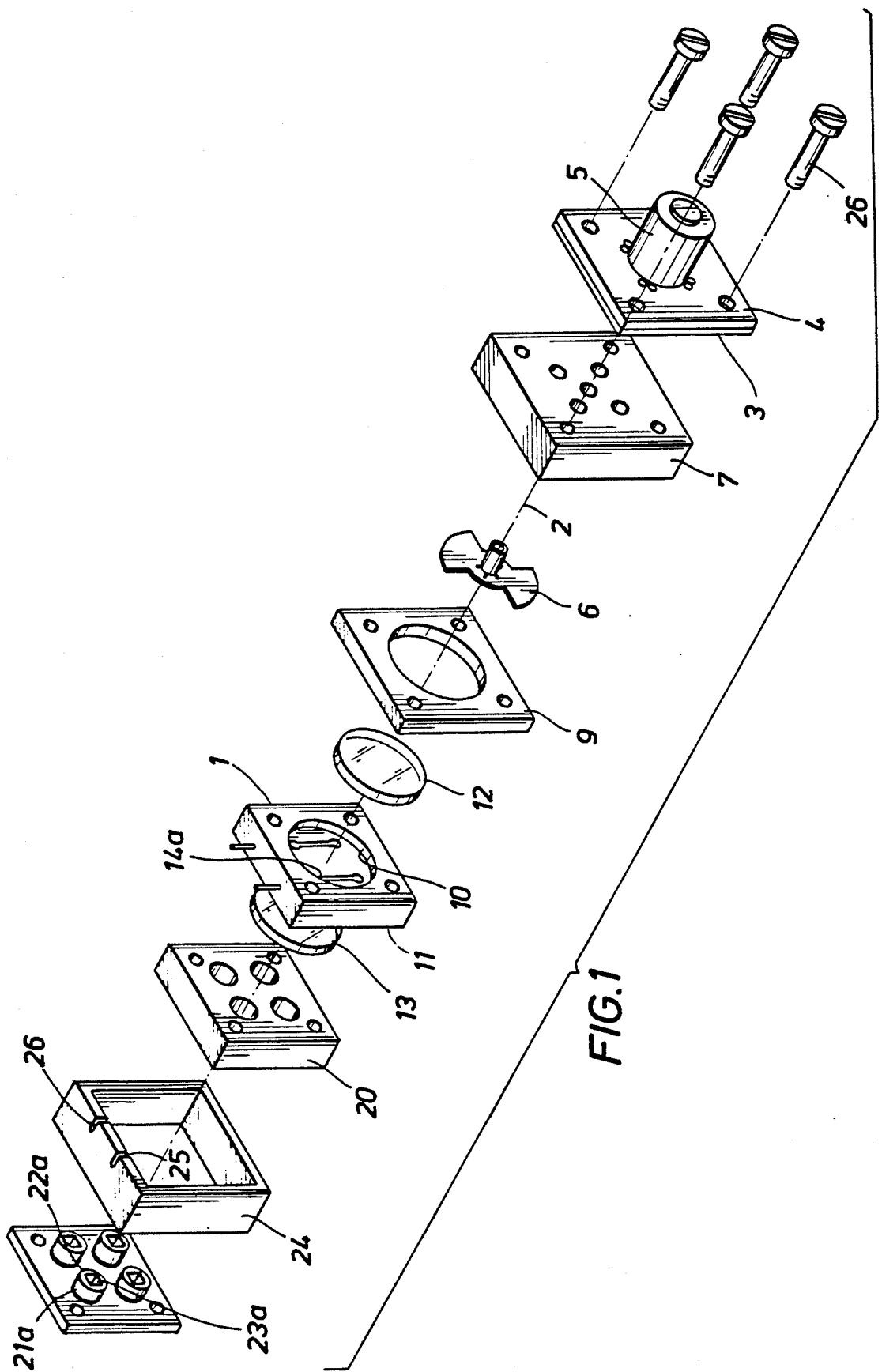

United States Patent [19]

Eckerbom et al.

[11] Patent Number: 5,326,973
[45] Date of Patent: Jul. 5, 1994

[54] DEVICE FOR GAS ANALYSIS

[75] Inventors: Anders Eckerbom, Bromma; Carl Hamilton, Kista; Robert Zyzanski, Gustavsberg, all of Sweden

[73] Assignee: Artema Medical AB, Sweden

[21] Appl. No.: 999,203

[22] Filed: Dec. 31, 1992

[30] Foreign Application Priority Data

Jan. 3, 1992 [SE] Sweden .................. 9200023-1

[51] Int. Cl.$^5$ ............................................ G01N 21/03
[52] U.S. Cl. ............................ 250/343; 250/345; 356/440; 128/719
[58] Field of Search .............. 250/343, 345; 356/246, 356/440; 128/719

[56] References Cited

U.S. PATENT DOCUMENTS

| | | | |
|---|---|---|---|
| 3,743,426 | 7/1973 | Steinberg | 250/345 |
| 4,370,553 | 1/1983 | Waycaster et al. | 250/343 |
| 4,496,840 | 1/1985 | Fabinski et al. | 250/345 |
| 5,130,544 | 7/1992 | Nilsson | 250/345 |
| 5,218,428 | 6/1993 | Hoult | 250/345 |

FOREIGN PATENT DOCUMENTS 0307625  3/1989  European Pat. Off. .

Primary Examiner—Paul M. Dzierzynski
Assistant Examiner—Drew A. Dunn
Attorney, Agent, or Firm—Pravel, Hewitt, Kimball & Krieger

[57] ABSTRACT

A device for gas analysis, which determines the content of two or more gases in a gas flow. The device includes at least one source for emission of two or more ray paths of radiation of a detectable wavelength, a cuvette device having an inlet and an outlet for uninterrupted gas flow, and a detector device for conversion of the radiation into an electrical signal. The source(s), cuvettes, and detectors are arranged such that ray paths emitted from the source pass through cuvettes containing gas and to detectors to permit analysis of two or more gases in a gas flow. In a preferred embodiment, the cuvette device includes a block having cuvettes positioned in each of the ray paths, which cuvettes are interconnected to form an unbroken conduit for gas flow from inlet to outlet.

13 Claims, 2 Drawing Sheets

DEVICE FOR GAS ANALYSIS

DESCRIPTION

The present invention relates to a device for a gas analysis, for assay of the content of two or more gases in a gas-flow. Such a device will be used in various fields of technique, and is particularly useful in medical care, for analysis of respiratory gases.

When a patient is laid in a respirator for surgery (anaesthesia) or in diseases which inhibit the normal breathing of the patient (intensive care), the normal control functions of the body are eliminated. These control functions normally control the breathing towards an equilibrium of gases dissolved in the blood (blood gases). For example, on physical effort, stress, changed metabolism and disease, said equilibrium is shifted, something which the body controls by changing frequency of breathing and/or tidal volume. For the operator of the respirator to be able to imitate this control function, information is required about the blood gas concentrations of the patients. Since the alveoles in the lungs are in close contact with the blood, and analysis of the respiratory gases gives a good estimate of the blood gas concentrations, and thereby important information for the treatment of the patient.

1. State of the Art

The patient gas analysis devices which are currently on the market mainly rely on the measuring principles mass spectroscopy, Raman scattering, infrared (IR) spectroscopy and crystal adsorption technique.

A device for gas analysis relying on IR spectroscopy employs the fact that many gases absorb IR radiation with a wavelength specific for the gas. The IR radiation in this instrument is generated by a source which transmits light in a broad spectrum, while the desired wavelength is filtered out by an optical band pass filter. With a detector, the radiation energy is converted into a proportional electric signal. For reasons of measuring technique one usually desires an intermittent flow of light which gives an alternating current signal from the sensor, obtained by introducing a shutter wing "chopper" into the ray path of the sensor. The choice of wavelength of analysis for a given analyte is very important, since it strongly effects the accuracy and response time of the measuring system. In practice the choice of wavelength of analysis is controlled by factors such as the adsorption of the analyte, and whether filters and detectors are commercially available for the chosen wavelength.

In a clinical context it is desired to monitor the concentration of carbon dioxide ($CO_2$), oxygen ($O_2$), laughing gas ($N_2O$) and in certain cases halogenated anaesthetics such as Halothane, Enflurane and Isoflourane. Due to this, with the increasing market interest for gas analysis, there has been a natural development towards instruments which can measure several gases. The halogenated anaesthetics have chemical similarities which cause them to have several overlapping absorption peaks in the IR spectrum. Together with the fact that only one anaesthetic is used at the time, this makes it possible to measure the usual anaesthetics with one and the same sensor. In the case where one wishes that the instrument should be able to automatically identify which anaesthetic is used, the anaesthetics however have to be measured on at least two wavelengths. Oxygen has no noticeable IR absorption, something which has commanded other measuring techniques for this gas.

Usually there is a need for devices for multiple gas analysis with two to four measuring wavelengths. On design of such a device for gas analysis, a number of methods have developed. Most common is so called time multiplexing, which is founded on sequential measuring of the adsorption for the respective wavelength. One can substitute for the shutter wing a filter wheel where the various band passage filters are mounted. The problem with this method is however that the filter wheel has to be put under thermostat control, since IR filters are strongly temperature sensitive. Another problem is that the filter wheel has to be completely symmetrical and must not be warped, since a change of the incoming angle also changes the filter characteristic. Another principle for multiple gas sensors is founded on the so called room multiplexing. This principle is shown by EP-A2-0,307,625, which describes an optical analyzer where radiation which passes through a measuring cell (cuvette), through which the sample gas is passing, is subsequently divided into three ray paths, for example with a three part mirror, whereupon each of these passes through one filter each and is detected in one detector each. The technique thus known is incorporated herein by reference, in particular with regard to detectors and wavelengths employed. However, a complicated device is obtained according to the art thus known, with high requirements for precision and a risk of measuring deviation by temperature deviation in the mirror.

2. Description of the Invention

An object of the invention is to avoid the drawbacks with known constructions, and achieving at an analysis device with a simple construction, short response time and good measuring accuracy. A further object is achieving at a device for a gas analysis with a compact design, without departing from the requirements of measuring accuracy, in particular for gases with a low absorbency.

According to the invention a device for a gas analysis is provided, for determination of the content of two or more gases in a gas flow, comprising at least one source for emission of two or more ray paths of radiation of a detectible wavelength, a cuvette device having an inlet and an outlet for the gas flow, a filter for transmission of radiation of a characteristic wavelength for the respective gas and a detector device comprising a plurality of detectors for conversion of the radiation into an electrical signal. The device for a gas analysis is characterized in that the cuvette device comprises a block with a number of through-going cuvettes in each of the ray paths, which cuvettes are interconnected by channels which connect the ends of the cuvettes, to the formation of an unbroken conduit for the gas flow from the inlet to the outlet, and in that a first and a second cuvette window, which cuvette windows are transparent for the radiation to be detected, are arranged at the block over each end of the cuvette device in the ray path from the source, adjacent to which second cuvette window the detectors are arranged.

The device according to the invention may make part of a monitoring device described in Swedish patent application No. 9103636-8, the contents of which are incorporated herein by reference.

According to a preferred embodiment of the invention, the connecting channels are taken up linearly or curve-shaped in the surface of the cuvette block, and thus substantially perpendicular to the direction of the ray path. It is also possible to arrange the channels as bores connecting the ends of the cuvettes along space diagonals. The channels are however preferably, for reasons of manufacturing technique and for facilitating the flow of gas, taken up, for example cut, as grooves in the surface of the cuvette block, and the channels are thereby additionally limited in the sideways direction by the cuvette window, which thus makes up one of the walls of the channels.

It is further preferred to arrange the cuvettes around a central axis in the cuvette block, which axis is parallel to the direction of the ray path, whereby preferably the central axis is co-axial with the rotational axis of a cutter wing, which intermittently breaks the ray path. The cuvettes, and thereby all elements pertaining to the respective ray path is thereby preferably placed symmetrically around this central axis. With for example an opening angle of the cutter wing of 90°, with four symmetrically placed cuvettes, measuring values can simultaneously be obtained from two cuvettes, and measuring values from the two others are obtained phase-shifted synchronously therewith.

The number of cuvettes may be adapted to the number of gases which are to be analyzed and/or the number of wavelengths of analysis which are required. In a corresponding manner the number of detectors may be selected. However, when less gases/wavelengths of analysis are needed than the number of cuvettes in an available device according to the invention, one or more cuvettes may be left unused. In a corresponding manner one or more detectors may be removed or left unused. Thus, the number of cuvettes is preferably four or a multiple thereof.

According to a further preferred embodiment of the invention the detectors are pyro-electric detectors.

The detector device preferably comprises a temperature-controlled plate on which the detectors are attached.

It is further preferred that the filters for transmission of radiation of a characteristic wavelength are attached to the respective detector.

Preferably the device for gas analysis according to the invention has a signal processing means wherein the signals are filtered by software and the filtration is done adaptively, based on the appearance of the measuring signal.

Figure 2:
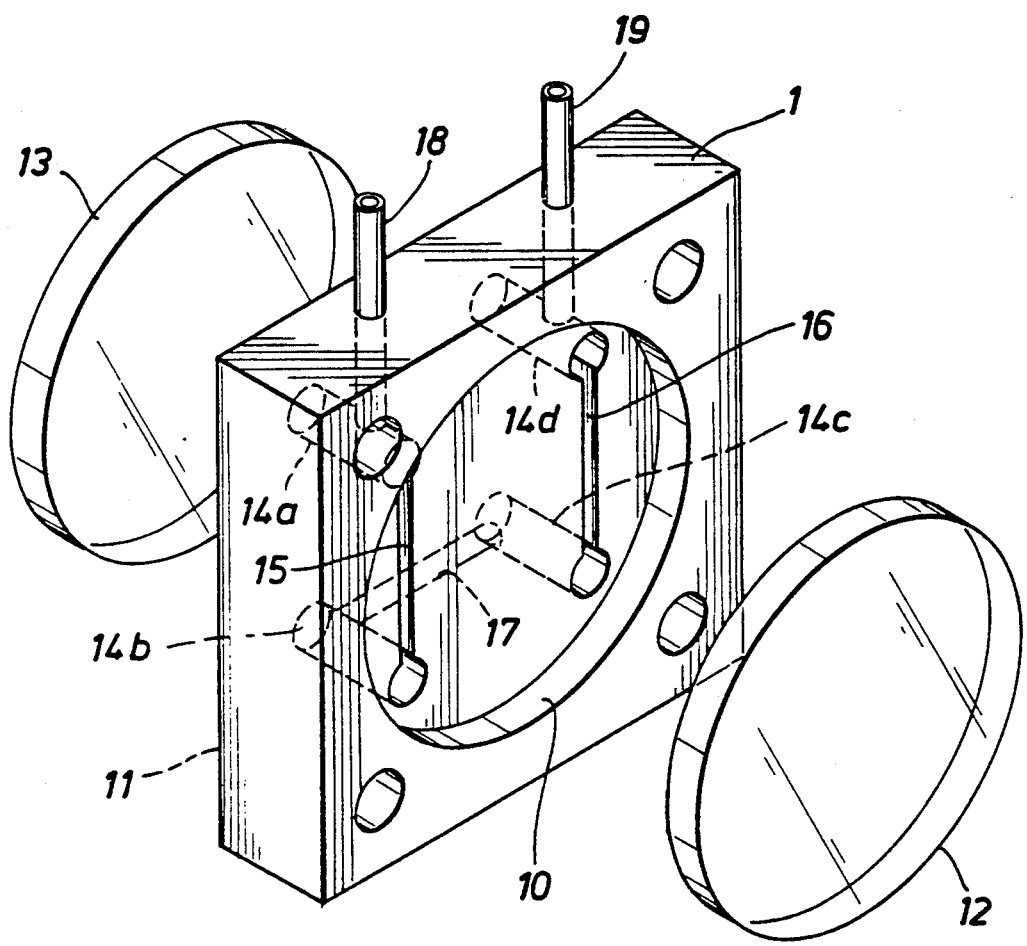

The invention is further described with a reference to enclosed drawings, wherein FIG. 1 is a schematic exploded view of a device for gas analysis according to a preferred embodiment of the invention, and FIG. 2 shows a cuvette device making part of the device for gas analysis according to FIG. 1.

Indications of the material for the different parts below refers to materials which are selected as particularly useful, but other materials may be selected by one skilled in the art.

In the drawings, a cuvette block is denoted 1. This has, in the chosen design, the shape of an right-angled block of aluminium, with a square cross section perpendicular to the direction of a ray path 2. The ray path beings in a source 3 for infrared light, concealed in the drawing, and mounted on a circuit 4. Four such sources of infrared light in total are mounted on a circuit board 4. From each of the sources, one ray path including ray path 2 shown in FIG. 1 and three further ray path run in parallel with ray path 2, to detectors 22. These ray paths are in the corners of a square.

On the card 4, an electric motor 5 is placed for rotation of a cutter wing 6 which has two diagonally opposite wing elements of phosphorus bronze with a 90° centre angle. The cutter wing opens in the position shown for ray path 2 and for the diagonally opposite ray path, while it breaks the other two ray paths. Before the cutter wing, the ray path passes a focusing block 87 shaped as an aluminium block with bores 8 for the four ray paths.

A distance plate 9 of plastic material (DELRIN) gives a temperature barrier between means placed before and after, and is a square slice having a circular opening 10 where the cutter wing 6 rotates.

The cuvette block 1 has in each of its square surfaces a circular recess 10, 11, in each of which the first 12 and a second 13 cuvette window of calcium fluoride $CaF_2$ may be placed, to sealing contact with the bottom surface of the respective recess. In the cuvette block four cuvettes 14a, 14b, 14c, 14d are placed in the respective ray path, and designed as through-going bores having their axes substantially in the respective ray path. The ends of the bores are sealed by the cuvette windows. In the bottom of the recess 10 two channels 15 and 16 are cut, which connect the cuvette 14a with 14b and 14c with 14d, respectively. Similarly a channel 17 is cut in the bottom of the recess 11 connecting the cuvette 14b with 14c. A pipe shaped inlet conduit 18 opens in the cuvette 14a close to the end thereof facing window 13, and close to the end of the cuvette 14d facing the same window, a pipe shaped outlet conduit 19 exits.

The cuvette widows 12 and 13 respectively, seal the open sides of channels 15 and 16, and 17, respectively. Thus a closed conduit is formed between elements 18, 14a, 15, 14b, 17, 14c, 16, 14d and 19.

In an embodiment given by means of example the inner diameters of the inlet and outlet conduits is 1 mm, the diameter of the cuvettes is 2 mm, and the width of the channels parallel to the respective cuvette glass is 1 mm, and their depths are 0.5 mm. The length of the cuvettes is 4.8 mm.

A distance block 20 of aluminium is placed immediately after the cuvette block. This has four holes in register with the four ray paths. In the holes, four detector holders 21a, 21b, 21c, 21d fit, placed on a heating block provided with a device, not shown, for holding detectors placed thereon at a constant elevated temperature. On the holder 21a a detector 22a for infrared light is attached, covered by a filter 23a, transmitting a wavelength which can be used for determination of concentration of a gas in sample gas flow, which is let in through the inlet conduit 18. Corresponding detectors 22b, 22c, 22d, but for different wavelengths are arranged on holders 21b, 21c and 21d.

The heating block can preferably be placed flatly against a circuit board provided with terminals for the detectors.

Finally, a temperature insulating frame 24 of polymer foam is designed to cover the heating block, the distance block and the cuvette block, in the assembled position of the device. Said frame has recesses 25, 26 for conduits 18, 19. Four screws 27 are arranged to hold the device gas analysis together, through corresponding holes. As an example of the outer dimensions of the device for analysis, the side of its square cross section may be 37 mm and the length in the direction of the ray path 32.5 mm, the motor 5 for the cutter wing not counted.

According to the preferred embodiment of the invention, up to four different wavelengths of analysis may be handled. The special cuvette block, which contains four separate cuvettes with connecting channels, makes it possible to reduce the size of the gas analysis device to less than half of the corresponding previously known constructions. The compact design means that the light scattering between the light source and the detector is reduced to a minimum, while a sufficient length of the cuvettes is maintained for achieving sufficient absorbency. A device for a gas analysis can, by its small size and small consumption of power, be mounted directly on the circuit board which handles the desired measurement and control.

Traditionally, IR measuring of gases for anaesthesia has required a long optical wavelength in the measuring cuvette. This is due to the fact that gases for anaesthesia have a relatively weak absorption in the wavelength field which available detectors permit. In later years however, pyroelectric detectors, which have a broader active spectrum, become more and more inexpensive. The pyro-electric detectors, however, have a higher intrinsic noise than traditional lead-selenide detectors. The noise problems caused by the detector can be handled by filtering the measuring signal. With strong filtering, one however risks that important curve information is lost, something which is not acceptable from a clinical point of view. To solve this problem, devices for a gas analysis have been provided with an adaptive digital filter realized in software. The adaptive filter "looks" at the measuring signal and selects a degree of filtration depending on the derivative of the curve—when the measuring signal is constant a stronger filter is selected than when the measuring signal varies. The chosen algorithm can comprise a number, for example five different so called finite impulse response (FIR) filter or infinite impulse response (IIR) filters, which the micro processor selects based on the appearance of the measuring signal. Adaptive filters in software are well-known to one skilled in the field of computerized measuring technique, and is described for example by Alan V. Oppenheim and Roland W. Shafer in Digital Signal Processing (Prentice Hall International, London 1975), and by Sven Eriksson and Lars Wanhammar: Tidsdiskreta filter del 1-3, (Time discreet filters part 1-3, in Swedish) Linkopings Tekniska Hoaskola 1978. The measuring signal obtained from the detectors can most closely be described as a triangle wave, the derivative of which being proportional to the radiation energy denoted I, transmitted through the measuring cuvette. To be able to compute this derivative, the micro processor has to enter into and convert the measuring signal analogue-to-digital, synchronously with the same. The measuring value thus obtained has thereupon to be put in relation to transmitted energy of radiation through the measuring cuvette without the measured gas, denoted $I_0$. According to Lambert-Beer's law the following then applies. $A = \log(I_0/I) \propto cl$ where $l$ = optical wavelength the measuring cuvette and $c$ = the concentration of the gas. (The sign $\propto$ denotes "is proportional to".) $I_0$ is, apart from temperature drift etc, constant for the device for a gas analysis and is computed by the microprocessor now and then shifting the pneumatics in the instrument thus that a different gas is lead into the measuring cuvette. After logarithmation according to Lambert-Beer's law, a measuring value is obtained proportional to the concentration of the gas. For achieving at a correctly calibrated measuring value, the program also has to comprise routines for calibration, compensation of pressure and other corrections.

We claim:

1. A device for analyzing at least two gases in a gas flow comprising:
   cuvette means having an inlet, an outlet and an unbroken gas flow conduit between the inlet and the outlet, the cuvette means including a cuvette block containing at least two cuvettes, which at least two cuvettes are interconnected end to end by channels to form the unbroken as flow conduit, and further including first and second cuvette windows, which cuvette windows are transparent to radiation,
   radiation source means for emitting at least two parallel and spaced apart ray paths of detectable wavelength radiation;
   filter means for transmitting radiation of a specific wavelength; and
   detector means comprising at least two detectors for converting the radiation into an electrical signal,
   wherein said first cuvette window is positioned between the radiation source means and the at least two cuvettes, and said second cuvette window is positioned between the at least two cuvettes and the at least two detectors;
   and wherein the at least two cuvettes and at least two detectors are positioned relative to the ray paths so that the radiation in each ray path passes through a cuvette to a corresponding detector for analysis of gas in the cuvette.

2. The device of claim 1, wherein the connecting channels are substantially perpendicular to the direction of the ray paths.

3. The device of claim 1, wherein the connecting channels are formed between the cuvette block and one of the cuvette windows by grooves in the surface of the cuvette block and covered with one of the cuvette windows.

4. The device of claim 1, wherein the at least two cuvettes are arranged around a central axis in the cuvette block, which axis is parallel to the direction of the ray paths.

5. The device of claim 4, wherein the central axis is co-axial with the rotational axis of a cutter wing, which cutter wing intermittently breaks the ray paths.

6. A device for analyzing at least two gases in a gas flow comprising:
   cuvette means having an inlet, an outlet and an unbroken gas flow conduit between the inlet and the outlet, the cuvette means including at least two cuvettes for containing gas flowing through the conduit;
   radiation source means for emitting at least two non-intersecting ray paths of detectable wavelength radiation; and
   detector means comprising at least two detectors for converting the radiation into an electrical signal,
   the at least two cuvettes and at least two detectors being positioned relative to the at least two ray paths so that the radiation in each ray path passes through a cuvette to a corresponding detector for analysis of gas in the cuvette.

7. The device of claim 6, wherein the number of cuvettes is four or a multiple thereof.

8. The device of claim 6, wherein the at least two detectors are pyro-electric detectors.

9. The device of claim 6, wherein the detector means comprises a temperature-controlled plate on which the at least two detectors are attached.

10. The device of claim 6, further comprising a signal processing means wherein the signals are adaptively filtered by software based on the appearance of the signal.

11. The device of claim 6, further comprising filter means for transmitting radiation of a specific wavelength.

12. The device of claim 11, wherein the filter means is attached to the at least two detectors.

13. The device of claim 6, wherein said cuvette means further includes first and second cuvette windows, which cuvette windows are transparent to the radiation, said first cuvette window positioned between the radiation source and the at least two cuvettes, and said second cuvette windows positioned between the at least two cuvettes, and the at least two detectors.

* * * * *